US010166388B2

(12) United States Patent
Isik et al.

(10) Patent No.: US 10,166,388 B2
(45) Date of Patent: Jan. 1, 2019

(54) METHOD FOR EXTRACTING TEMPORAL FEATURES FROM SPIKE-LIKE SIGNALS

(71) Applicant: MED-EL Elektromedizinische Geraete GmbH, Innsbruck (AT)

(72) Inventors: Michael Isik, München (DE); Werner Hemmert, Garching (DE)

(73) Assignees: MED-EL Elektromedizinische Geraete GmbH, Innsbruck (AT); Technische Universität München, München (DE)

( * ) Notice: Subject to any disclaimer, the term of this patent is extended or adjusted under 35 U.S.C. 154(b) by 223 days.

(21) Appl. No.: 15/027,307

(22) PCT Filed: Oct. 6, 2014

(86) PCT No.: PCT/US2014/059218
§ 371 (c)(1),
(2) Date: Apr. 5, 2016

(87) PCT Pub. No.: WO2015/054090
PCT Pub. Date: Apr. 16, 2015

(65) Prior Publication Data
US 2016/0235987 A1    Aug. 18, 2016

Related U.S. Application Data

(60) Provisional application No. 61/887,551, filed on Oct. 7, 2013.

(51) Int. Cl.
*A61N 1/36*        (2006.01)
(52) U.S. Cl.
CPC .............................. *A61N 1/36032* (2013.01)

(58) Field of Classification Search
CPC .... A61N 1/36; A61N 1/0541; A61N 1/36036; A61N 1/36038; A61N 1/36032
See application file for complete search history.

(56) References Cited

U.S. PATENT DOCUMENTS 3,889,108 A *  6/1975  Cantrell ............ H03H 21/0043
                                            327/553
7,225,027 B2 *  5/2007  Zeng ..................... H04H 20/48
                                            607/137
(Continued)

FOREIGN PATENT DOCUMENTS

WO    WO 2013/009805         1/2013

OTHER PUBLICATIONS

International Searching Authority, Authorized Officer Blaine R. Copenheaver, International Search Report and the Written Opinion for PCT/US2014/059218, dated Jan. 21, 2015, 15 pages.

*Primary Examiner* — Alyssa M Alter
(74) *Attorney, Agent, or Firm* — Sunstein Kann Murphy & Timbers LLP

(57) ABSTRACT

A system and method for the evaluation of hearing implant signal processing is described. A cochlear implant signal processor converts a speech signal input into multi-channel stimulation pulse sequences for a cochlear implant electrode array. A temporal feature processing module extracts temporal feature information from the stimulation pulse sequences. A speech recognition engine evaluates the temporal information using automatic speech recognition to produce speech recognition outputs corresponding to the speech signal input.

20 Claims, 4 Drawing Sheets

(56) References Cited

U.S. PATENT DOCUMENTS

| | | |
|---|---|---|
| 7,231,257 B2 | 6/2007 | McDermott et al. |
| 7,310,558 B2 * | 12/2007 | Van Hoesel ....... A61N 1/36036 |
| | | 607/57 |
| 2007/0270949 A1 | 11/2007 | Paolini et al. |
| 2009/0018614 A1 | 1/2009 | Zierhofer |
| 2014/0100630 A1 * | 4/2014 | Hemmert ........... A61N 1/36032 |
| | | 607/57 |
| 2014/0348337 A1 * | 11/2014 | Franck .................... H04R 3/12 |
| | | 381/59 |

* cited by examiner

METHOD FOR EXTRACTING TEMPORAL FEATURES FROM SPIKE-LIKE SIGNALS

This application is a National Phase Entry of Patent Cooperation Treat Application PCT/US2014/059218, filed Oct. 6, 2014, which in turn claims priority from U.S. Provisional Patent Application 61/887,551, filed Oct. 7, 2013, both of which are incorporated herein by reference in their entireties.

TECHNICAL FIELD

The present invention relates to cochlear, auditory brainstem, midbrain or cortical implants and automatic speech recognition systems and evaluation of their signal coding strategies.

BACKGROUND ART

A normal ear transmits sounds as shown in FIG. 1 through the outer ear 101 to the tympanic membrane (eardrum) 102, which moves the bones of the middle ear 103, which in turn vibrate the oval window and round window openings of the cochlea 104. The cochlea 104 is a long narrow duct wound spirally about its axis for approximately two and a half turns. The cochlea 104 includes an upper channel known as the scala vestibuli and a lower channel known as the scala tympani, which are connected by the cochlear duct. The scala tympani forms an upright spiraling cone with a center called the modiolar bone where the spiral ganglion cells of the acoustic nerve 113 reside. In response to received sounds transmitted by the middle ear 103, the fluid filled cochlea 104 functions as a transducer to generate electric pulses that are transmitted by the cochlear nerve 113 to the brain. Hearing is impaired when there are problems in the ability to transduce external sounds into meaningful action potentials along the neural substrate of the cochlea 104.

In some cases, hearing impairment can be addressed by a cochlear implant (CI), a brainstem-, midbrain- or cortical implant that electrically stimulates auditory nerve tissue with small currents delivered by multiple electrode contacts distributed along an implant electrode. For cochlear implants, the electrode array is inserted into the cochlea. For brainstem, midbrain and cortical implants, the electrode array is located in the auditory brainstem, midbrain or cortex, respectively. FIG. 1 shows some components of a typical cochlear implant system where an external microphone provides an audio signal input to an external signal processor 111 which implements one of various known signal processing schemes. For example, signal processing approaches that are well-known in the field of cochlear implants include continuous interleaved sampling (CIS) digital signal processing, channel specific sampling sequences (CSSS) digital signal processing (as described in U.S. Pat. No. 6,348,070, incorporated herein by reference), spectral peak (SPEAK) digital signal processing, fine structure processing (FSP) and compressed analog (CA) signal processing. The processed signal is converted by the external signal processor 111 into a digital data format, such as a sequence of data frames, for transmission by an external coil 107 into a receiving stimulator processor 108. Besides extracting the audio information, the receiver processor in the stimulator processor 108 may perform additional signal processing such as error correction, pulse formation, etc., and produces a stimulation pattern (based on the extracted audio information) that is sent through electrode lead 109 to an implanted electrode array 110. Typically, the electrode array 110 includes multiple stimulation contacts on its surface that provide selective electrical stimulation of the cochlea 104.

Improving coding strategies for cochlear implants requires speech perception tests with large numbers of patients, which are very time demanding and depend to a large extent on the individuals. If changes involve new hardware features of the implant, these tests are not possible before the new devices are implanted. Performance improvements are difficult to prove, they require subjective speech tests with large numbers of cochlear implant patients.

The coding strategies for generating the data signals for cochlear implant systems long neglected any fine-grained temporal information, as did automatic speech recognition (ASR) systems. This was because of the notion that the spectral envelopes of the stimulation pulses code all relevant information required for speech understanding. In addition, there simply were not recognized techniques to extract temporal speech features.

The development of coding strategies for cochlear implants mainly relies on an educated guess as to how to improve temporal features of cochlear implant coding strategies and time consuming tests on patients. The evaluation of the rate place code only was proposed to evaluate coding strategies in WO 2013/009805. As shown in FIG. 2, a CI signal processor 201 generated stimulation signals for an implanted electrode array. Feature adjustment module 202 adjusted the feature resolution of the CI stimulation signals to produce a corresponding sequence of cochlear stimulation vectors for automatic speech recognition (ASR) processing. ASR vector pre-processor 203 mapped the cochlear stimulation vectors into corresponding vectors for ASR and ASR Engine 204 evaluated those using ASR techniques. But the rate place code exploited in that invention does not preserve information about the temporal fine structure.

In research, several methods to extract temporal fine-structure information have been described. Oded Ghitza, *Auditory Nerve Representation as a Front-End for Speech Recognition in a Noisy Environment*, Computer Speech & Language, Volume 1, Issue 2, December 1986, Pages 109-130 (incorporated herein by reference) suggested that an ensemble interval histogram might be used for temporal speech feature extraction. Hugh and Campbell L. Searle, *Time-Domain Analysis of Auditory-Nerve Fiber Firing Rates*, Journal of the Acoustical Society of America, 85(S1): S534, 1989 (incorporated herein by reference) described extracting temporal features using inter-peak interval histograms. Average localized synchronized rate (ALSR) was used by Young and Sachs, *Representation of Steady-State Vowels in the Temporal Aspects of the Discharge Patterns of Populations of Auditory-Nerve Fibers*, Journal of the Acoustical Society of America, 66(5):1381-1403, 1979 (incorporated herein by reference).

SUMMARY

Embodiments of the present invention are directed to arrangements for evaluating signal processing strategies used in cochlear implants. A cochlear implant signal processor is configured to convert a speech signal input into multi-channel stimulation pulse sequences for a cochlear implant electrode array. A temporal feature processing module extracts temporal feature information from the stimulation pulse sequences. A speech recognition engine evaluates the temporal feature information using automatic speech recognition to produce speech recognition outputs corresponding to the speech signal input.

In further specific embodiments, the temporal feature processing module can include a windowing module that processes temporal information from multiple input channels in short time slices. There may be a temporal information extraction module configured to extract the temporal feature information using a short term spectrum calculation.

Specific embodiments can also include one or more specific information limiting modules to filter out unwanted information and reduce the complexity of the extracted temporal information in order to facilitate the speech recognition process using a reduced feature set. Thus a temporal feature limiting module may be configured to limit the temporal feature information represented by a short term spectrum by discarding phase information and preserving magnitude information only. In addition or alternatively, a temporal feature limiting module can be configured to remove unwanted frequency content such as frequencies greater than some given channel maximum for each signal channel when extracting the temporal feature information. For example, a low pass brick-wall filter and/or a band pass filter (e.g., within the initial filter bank) can be used for that purpose. There also can be a temporal information aggregation module configured to aggregate temporal information across signal channels. A decorrelation module may be configured to transform the temporal feature information into a more physiological space such as the mel spectrum and a channel limiting module may be configured to provide the n-most significant coefficients as a limited feature set to the ASR engine for speech recognition.

Embodiments of the present invention enable direct evaluation of the stimulation pulse sequences produced by the cochlear implant signal processor and also of auditory nerve spike trains. These auditory nerve spike trains can be produced by physiological measurements, by a computer model of the intact inner ear, by a simplified model of auditory processing (e.g., for automatic speech recognition applications), and/or by a neural response model for modeling discharge trains of auditory neurons to electrically stimulated auditory nerve responses. In the last case, the evaluation arrangement can also evaluate how much temporal information can be conveyed to the neuronal system by the coding strategy and how much information is lost in the neuronal system.

DETAILED DESCRIPTION

Various embodiments of the present invention are directed to arrangements for testing and optimizing coding strategies of cochlear implants (CI) based on extracting temporal feature information conveyed by the stimulation pulse sequences and evaluating the significance of these temporal features with automatic speech recognition (ASR). In contrast to conventional ASR and CI speech coding strategies relying on spectral features (or envelope extraction), the extraction of the temporal feature information is based on analysis of the fine structure information of the CI stimulation pulse sequence. The frequency spectrum of each individual stimulation pulse is so broad that important temporal information is masked regarding the signal generating system, which usually has a much narrower bandwidth. The temporal feature extraction described herein removes unwanted higher harmonics in the frequency spectrum of the stimulation pulse sequence while still preserving useful spectral components.

Besides stimulation pulse sequences for cochlear implants, embodiments of the present invention also can be applied to evaluate temporal information conveyed by other signal forms such as neuronal spike trains (e.g., from auditory models) and other signal producing systems and other pattern classification problems. Embodiments also are applicable to improve automatic speech recognition systems (ASR) using a combination of temporal features with conventional speech features (such as MFCC or conventional rate place features).

Figure 1:
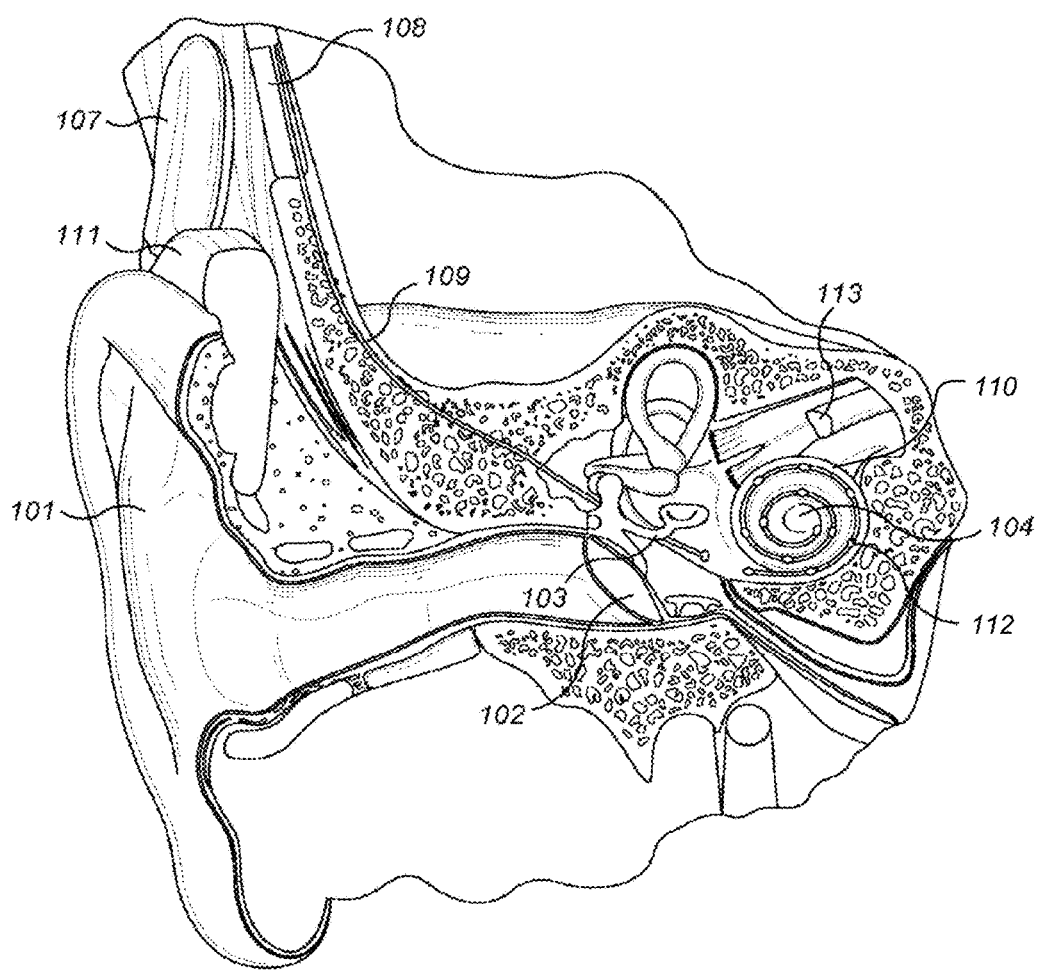
FIG. 1 shows various anatomical structures of a typical human ear and a cochlear implant system.
Figure 2:
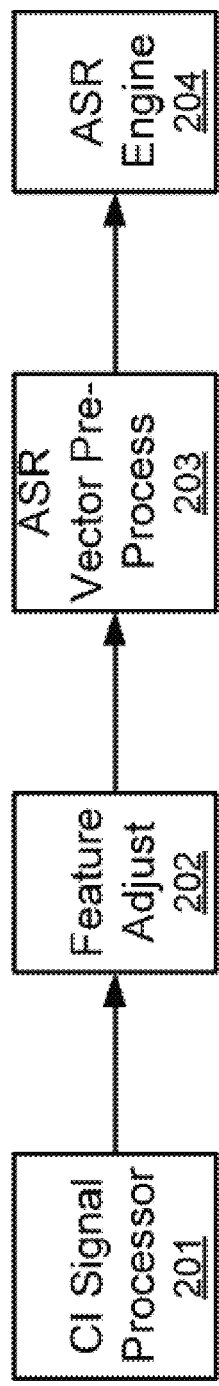
FIG. 2 shows various functional blocks in a cochlear implant signal processing arrangement according to the prior art.
Figure 3:
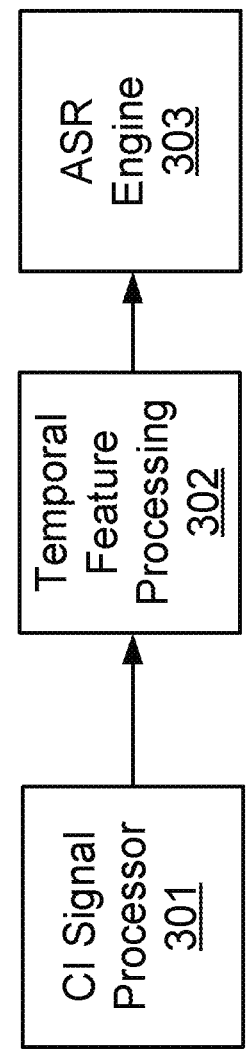
FIG. 3 shows various functional blocks in a cochlear implant signal processing arrangement according to an embodiment of the present invention.

FIG. 3 shows various basic functional blocks in a cochlear implant signal processing and evaluation arrangement according to an embodiment of the present invention. A cochlear implant signal processor 301 converts a speech signal input into multi-channel stimulation pulse sequences for a cochlear implant electrode array. A temporal feature processing module 302 extracts temporal feature information from the stimulation pulse sequences produced by the signal processor 301 as explained below at greater length. A speech recognition engine 303 evaluates the temporal feature information using automatic speech recognition to produce speech recognition outputs corresponding to the speech signal input.

In the specific case of CI systems that use a continuous interleaved sampling (CIS) coding strategy, the CI signal processor 301 first filters the input sound by a bank of band-pass filters. In each filter band, the signal processor 301 extracts the signal envelope (e.g., using a Hilbert transform or rectification followed by low-pass filtering), and then samples the signal envelope with a fixed CIS frame-rate to produce bi-phasic stimulation pulse sequences that are delivered to the electrode contacts of the implanted electrode array. Some temporal fine-structure coding strategies such as FSP or FS4 try to preserve more temporal information than just the pure band pass envelope by using the phase-locking principle that is observed in auditory spike trains. This can be based on sampling of the rectified band pass filter outputs or by zero-crossing detection. Such fine structure coding strategies, depending on their exact realization, more or less give up the CIS frame rate so that there is no fixed sampling rate and therefore no fixed Nyquist frequency.

The speech recognition engine 303 can be based on a multi-layer perceptron for phoneme classification followed by a trained ASR back end for final utterance classification. The speech recognition results from the speech recognition engine 303 can include the speech recognition scores and confusion matrices that indicate the quality of speech coding and are evaluated in order to improve cochlear implant systems.

The extracted temporal feature information can be used to analyze which information is coded by the stimulation pulse sequences. Using appropriate stimuli allows analysis of the quality of pitch coding in the time domain (both pure tones and more complex signals) and/or the quality of amplitude modulation coding (amplitude modulated signals). In addition to such specific analysis, a comprehensive analysis can be applied which evaluates the importance of the temporal features for speech coding using the speech recognition engine 303.

Figure 4:
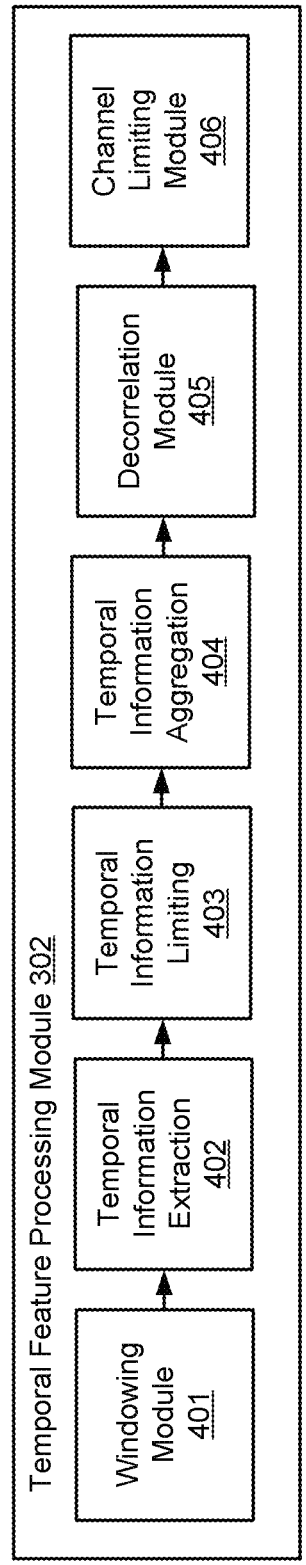
FIG. 4 shows various functional details of the temporal feature processing module according to one embodiment of the present invention.
Figure 5:
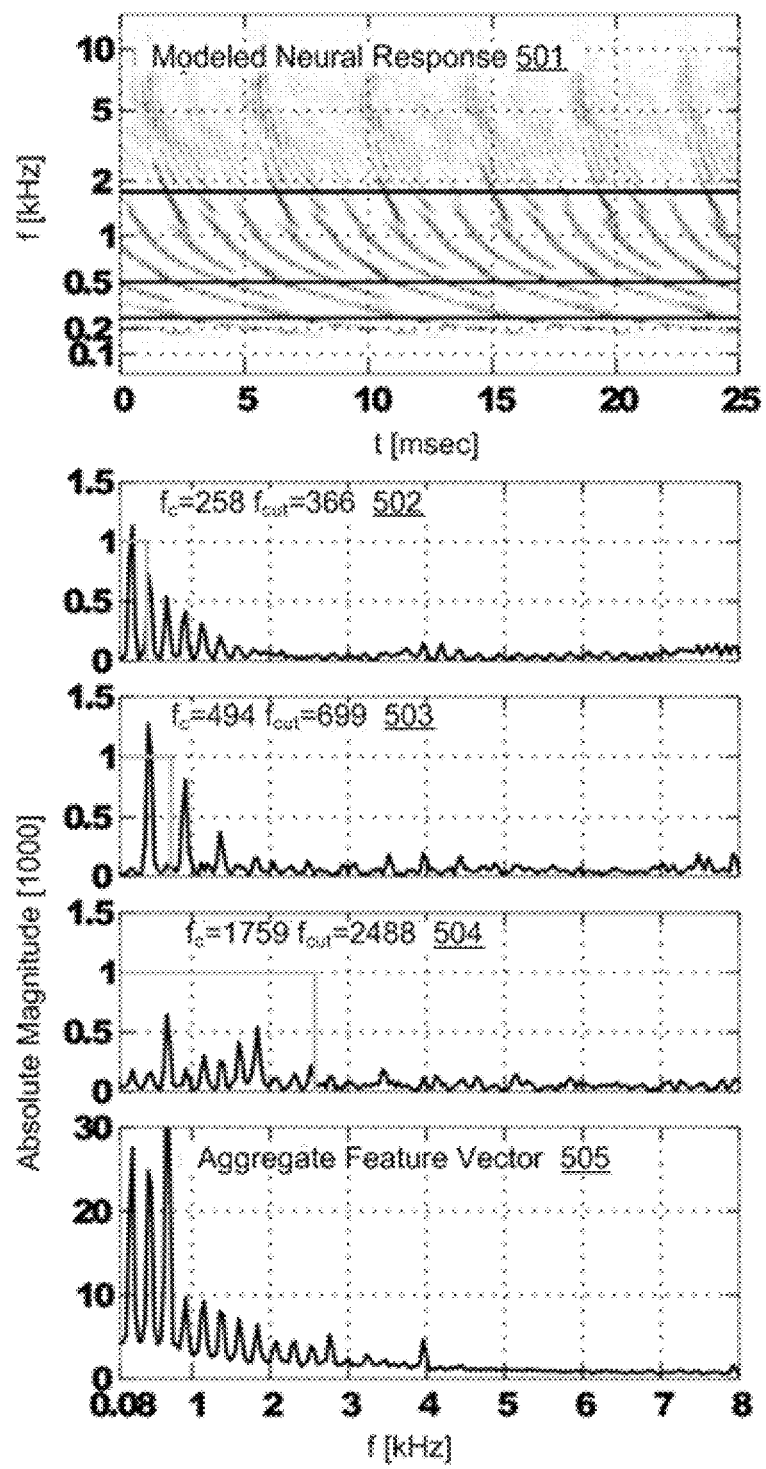
FIG. 5 shows an example of signal processing by the temporal feature processing module of multichannel nerve responses from a cochlea model in three channels and the aggregation of the temporal information across the channels.

FIG. 4 shows various functional details of the temporal feature processing module 302 and FIG. 5 shows various exemplary signals according to one specific embodiment of the present invention. To extract the temporal feature information in signals such as CIS stimulation pulses, the temporal feature processing module 302 analyzes the stimulation pulse sequences (e.g., a Dirac pulse train at the CIS frame rate) and ignores the bi-phasic pulse shapes. The top waveform shown in FIG. 5 is a modeled neural response 501 from an auditory model as input into the temporal feature processing module 302.

An initial windowing module 401 extracts time frames of each input signal channel by applying a sliding window algorithm (e.g., a sliding Hamming window of 1-1000 msec, preferably about 25 msec), and then temporal information extraction module 402 extracts temporal feature information from each windowed signal frame. For example, the temporal information extraction module 402 can be configured to extract short term spectrum information using a short-term Fourier transformation. The middle waveforms in FIG. 5 show specific examples of such temporal information feature signals 502, 503, and 504 for three different frequencies. For auditory neuronal spike train signals, the temporal information extraction module 402 can extract and analyze the temporal feature information for single or multiple neuronal spike trains in the auditory nerve (either from physiological recordings or derived from computational inner ear models). These neuronal spike trains represent the response of single or multiple auditory nerve fibers from a specific cochlear location which corresponds to a specific characteristic frequency (502: 258 Hz, 503: 494 Hz, 504: 1759 Hz).

In theory, the temporal feature information produced by the temporal information extraction module 402 might be applied to a (very large) speech corpus to train a speech recognition engine 303 designed to handle such high dimensional data. But existing ASR back ends are not able to handle such high dimensional data so a temporal information limiting module 403 reduces the signal dimensionality by removing unneeded frequency information, discarding unnecessary phase information, and keeping only magnitude spectra. Sounds reaching a specific cochlear location are processed by a nonlinear filter structure in the inner ear with a very steep low-pass slope. For the specific nerve fiber, the temporal information limiting module 403 can use, for example, low pass filters that are each configured based on the corresponding high-frequency cut-off frequency of the band pass filter of their input signal channel which discard all frequencies above the high-frequency roll-off of each band-pass filter. In higher frequency channels, low-pass filters with even lower cut-off frequencies might be used by the temporal information limiting module 403, especially if the average sampling frequency is less than the center frequency.

The temporal information limiting module 403 specifically can use a brick-wall filter with a cut-off frequency that is half an octave higher than the band pass filter frequency of the corresponding frequency channel. The temporal information feature signals 502, 503, and 504 shown in FIG. 5 show a grey line to represent this cut off of unneeded frequency information by the temporal information limiting module 403. Such an approach preserves valuable information about frequencies around the center frequency of each band pass channel as well as slow modulations within the specific signal channel. Harmonics and other higher frequency components arising from the broad spectrum of the stimulation pulses are removed by the temporal information limiting module 403. One or more notch filters can be used to suppress the stimulation frequency used by the CI system. The temporal information limiting module 403 can also extract temporal feature information from neuronal spike trains that are elicited by electrical stimulation with a cochlear implant.

Temporal information aggregation module 404 further reduces dimensionality of the temporal feature information by aggregating the information of all the multiple signal channels by summing the magnitude spectra in each time window to yield an to produce a single feature vector such as the aggregate feature 505 shown in FIG. 5. Other aggregation methods are also feasible, which include a phase correction across the frequencies followed by the sum of the complex spectra.

Decorrelation module 405 transforms the temporal feature information into a more physiological space such as a mel-frequency (or Greenwood scaled) spectrum conventionally used in ASR. For example, the decorrelation module 405 may specifically use one or more of discrete cosine transform (DCT), principal component analysis (PCA), linear discriminant analysis (LDA), Karhunen-Loève-Transformation (KLT). A channel limiting module 407 can keep and output the first n-most significant coefficients (e.g., n=35) to the speech recognition engine 303.

The evaluation of CI coding strategies with the methods disclosed here is relatively fast and enables sped-up innovation cycles by orders of magnitude. By testing complex and realistic hearing scenarios such as clean speech, speech in noise, and speech in reverberant rooms a detailed analysis of recognition errors can be performed (e.g., which phonemes are most likely to be confused) which in turn helps to identify and correct weaknesses in coding strategies.

The comparison of speech recognition scores of a new coding strategy versus a reference strategy provides quantitative data on how well temporal features relevant for speech understanding are coded. Before now, the evaluation of temporal feature information is typically restricted to sound localization cues, but embodiments of the present invention now allow the direct evaluation of speech information coded by fine structure coding strategies used in cochlear implants. The speech features coded in the time domain are thought to be more robust to noise so such embodiments also can improve the quality and noise robustness of ASR systems.

Embodiments of the invention may be implemented in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A system for cochlear implant signal processing, the system comprising:
    a cochlear implant signal processor configured to convert a speech signal input into multi-channel stimulation pulse sequences for a cochlear implant electrode array;
    a temporal feature processing module configured to extract temporal feature information based on fine structure information from the stimulation pulse sequences; and
    a speech recognition engine configured to evaluate the temporal feature information using automatic speech recognition to produce speech recognition outputs corresponding to the speech signal input.

2. The system according to claim 1, wherein the temporal feature processing module includes a temporal feature extraction module configured to extract the temporal feature information using a short term spectrum calculation.

3. The system according to claim 2, wherein the temporal feature processing module includes a temporal information limiting module configured to limit temporal feature information represented by a short term spectrum by discarding phase information and preserving magnitude information.

4. The system according to claim 1, wherein the temporal feature processing module includes a temporal information limiting module configured to remove frequency content greater than some given channel maximum for each signal channel to extract the temporal feature information.

5. The system according to claim 4, wherein the temporal information limiting module uses a low pass brick-wall filter to remove frequency content.

6. The system according to claim 5, wherein the temporal information limiting module uses a band pass filter with the brick-wall filter.

7. The system according to claim 4, wherein the temporal information limiting module uses a low pass filter to remove frequency content.

8. The system according to claim 1, wherein the temporal feature processing module includes a temporal information aggregation module configured to aggregate temporal information across signal channels when extracting the temporal feature information.

9. The system according to claim 1, wherein the temporal feature processing module includes decorrelation module configured to transform the temporal feature information into a different physiological space.

10. The system according to claim 1, wherein the temporal feature processing module includes a channel limiting module configured to output a set of n-most significant coefficients for speech recognition.

11. A method for the evaluation of cochlear implant signal processing, the method comprising:
    converting a speech signal input into multi-channel stimulation pulse sequences for a cochlear implant electrode array;
    extracting temporal feature information based on fine structure information from the stimulation pulse sequences; and
    evaluating the temporal feature information to produce speech recognition outputs corresponding to the speech signal input.

12. The method according to claim 11, wherein extracting the temporal feature information includes using a short term spectrum calculation.

13. The method according to claim 12, wherein the temporal feature information in the short term spectrum is limited by discarding phase information and preserving magnitude information.

14. The method according to claim 11, wherein extracting the temporal feature information includes removing frequency content greater than some given channel maximum for each signal channel.

15. The method according to claim 14, wherein a low pass brick-wall filter is used for removing frequency content.

16. The method according to claim 15, wherein a band pass filter is used with the brick-wall filter.

17. The method according to claim 14, wherein a low pass filter is used for removing frequency content.

18. The method according to claim 11, wherein extracting the temporal feature information includes aggregating temporal information across signal channels.

19. The method according to claim 11, wherein extracting the temporal feature information includes decorrelating the temporal feature information based on a transform into a different physiological space.

20. The method according to claim 11, wherein extracting the temporal feature information includes performing channel limiting to output a set of n-most significant coefficients for speech recognition.

* * * * *